United States Patent [19]

Saito et al.

[11] Patent Number: 5,393,332
[45] Date of Patent: Feb. 28, 1995

[54] COLOR DEVELOPER FOR PRESSURE-SENSITIVE RECORDING SHEETS

[75] Inventors: Toranosuke Saito; Takashi Ishibashi; Eiji Kawabata, all of Osaka; Masato Tanaka; Toshio Kimura, both of Hyogo, all of Japan

[73] Assignees: Sanko Kaihatsu Kagaku Kenkyusho, Osaka; Kanzaki Paper Manufacturing Co., Ltd., Tokyo, both of Japan

[21] Appl. No.: 164,483

[22] Filed: Dec. 9, 1993

Related U.S. Application Data

[62] Division of Ser. No. 994,499, Dec. 21, 1992, abandoned.

[30] Foreign Application Priority Data

Dec. 27, 1991 [JP] Japan ................................. 358093

[51] Int. Cl.⁶ .................... C09D 11/00; C07C 51/15
[52] U.S. Cl. .................... 106/21 R; 562/424
[58] Field of Search .................... 106/21 R, 21 A; 562/424

[56] References Cited

U.S. PATENT DOCUMENTS

| | | | |
|---|---|---|---|
| 2,244,769 | 6/1941 | Doelling | 562/424 |
| 2,252,662 | 8/1941 | Reiff | 562/424 |
| 2,453,105 | 11/1948 | Wolthuis | 562/424 |
| 2,685,600 | 8/1954 | Morris | 562/424 |
| 2,807,643 | 9/1957 | Hartley | 562/424 |
| 2,824,892 | 2/1958 | Barkley | 562/424 |
| 3,704,315 | 11/1972 | Strang | 562/424 |
| 3,825,593 | 7/1974 | Meek | 562/424 |
| 3,896,255 | 7/1975 | Kato et al. | 428/411 |
| 3,900,215 | 8/1975 | Kato et al. | 282/27.5 |
| 3,934,070 | 1/1976 | Kimura et al. | 428/342 |
| 3,983,292 | 9/1976 | Saito et al. | 428/306 |
| 4,063,873 | 7/1977 | Huffman | 562/424 |
| 4,234,212 | 11/1980 | Kato et al. | 282/27.5 |
| 4,289,332 | 9/1981 | Kato | 282/27.5 |
| 5,075,278 | 12/1991 | Vassiliades | 503/210 |
| 5,141,557 | 8/1992 | Higashiyama | 106/21 R |
| 5,164,001 | 11/1992 | Saito et al. | 106/21 R |
| 5,250,108 | 10/1993 | Tanaka et al. | 106/21 A |

FOREIGN PATENT DOCUMENTS

| | | |
|---|---|---|
| 0186354 | 2/1986 | European Pat. Off. |
| 0219302 | 2/1987 | European Pat. Off. |
| 0330685 | 4/1989 | European Pat. Off. |
| 436379A | 12/1990 | European Pat. Off. |
| 1042603 | 11/1958 | Germany |
| 521327 | 1/1952 | Japan |
| 51-25174 | 7/1976 | Japan |
| 52-7372 | 1/1977 | Japan |
| 52-29205 | 8/1977 | Japan |
| 6049118 | 10/1979 | Japan |
| 6054196 | 11/1980 | Japan |
| 63-165341 | 7/1988 | Japan | 562/424 |
| 1145189 | 6/1989 | Japan |
| 1258640 | 10/1989 | Japan | 562/424 |
| 2500428 | 2/1990 | Japan |
| 285231 | 3/1990 | Japan |
| 2122977 | 5/1990 | Japan |
| 2142747 | 5/1990 | Japan |
| 2204472 | 8/1990 | Japan |
| 2290829 | 11/1990 | Japan | 562/424 |
| 2017090 | 3/1979 | United Kingdom |
| 8900506 | 1/1989 | WIPO |

Primary Examiner—Helene Klemanski
Attorney, Agent, or Firm—Baker & Daniels

[57] ABSTRACT

Herein disclosed is a method for preparing a nuclear-substituted salicylic acid or a metal salt thereof represented by the following general formula (1):

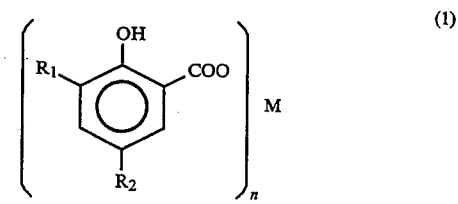

(1)

[wherein $R_1$ and $R_2$ each represents a t-butyl group, a t-amyl group, a t-octyl group, an isononyl group or an isododecyl group, provided that at least one of $R_1$ and $R_2$ represents an isononyl group or an isododecyl group; M represents a hydrogen atom or a metal atom; and n is the atomic valency of the metal atom M] which comprises the step of subjecting, to a Kolbe-Schmitt reaction, an alkali metal salt of a nuclear-substituted phenol represented by the following general formula (2):

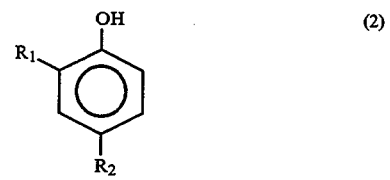

(2)

[wherein $R_1$ and $R_2$ are the same as those defined above] in which 100 to 50% of the alkali metal salt is potassium salt and 0 to 50% thereof is sodium salt, in a substantially water-insoluble solvent as a reaction medium. The method makes it possible to improve the yield of the specific nuclear-substituted salicylic acid and metal salts thereof and to provide such products having high purity without any post-treatment. The compounds can be used in color developers for pressure-sensitive recording sheets without any additional purification treatment.

11 Claims, No Drawings

COLOR DEVELOPER FOR PRESSURE-SENSITIVE RECORDING SHEETS

This is a division of application Ser. No. 07/994,499, filed Dec. 21, 1992, now abandoned.

BACKGROUND OF THE INVENTION (a) Field of the Invention

The present invention relates to a method for preparing a nuclear-substituted salicylic acid or a metal salt thereof. More particularly, the present invention relates to a method for preparing a nuclear-substituted salicylic acid or a metal salt thereof from an alkali metal salt of a specific nuclear-substituted phenol by a Kolbe-Schmitt reaction. The nuclear-substituted salicylic acid or the metal salt thereof may be used in wide variety of fields such as antibacterial agents, additives for lubricating oils and plastics and color developing agents-for pressure-sensitive recording sheets.

(b) Description of the Prior Art

Specific nuclear-substituted salicylic acids or metal salts thereof are useful as, in particular, color developing agents for pressure-sensitive recording sheets or materials for preparing the same. Several methods for preparing these compounds have already been proposed. Among these, those making use of Kolbe-Schmitt reactions which are also concerned with the present invention are disclosed in, for instance, Japanese Examined Patent Publication (hereinafter referred to as "J. P. KOKOKU") No. Sho 51-25174, Japanese Unexamined Patent Publication (hereinafter referred to as "J. P. KOKAI") Nos. Hei 1-145189, Hei 2-85231, Hei 2-122977, Hei 2-142747 and Hei 2-204472. However, these patents never recognize the difference in the reaction rates or the reaction yields of the Kolbe-Schmitt reactions, to which the present invention particularly relates, between kinds of alkali metals and, in fact, sodium is exclusively selected and used simply for economical reason.

When nuclear-substituted salicylic acids or metal salts thereof are prepared by the use of Kolbe-Schmitt reactions, the reaction product inevitably includes the unreacted nuclear-substituted phenol in greater or lesser degree. Therefore, if highly pure nuclear-substituted salicylic acids or metal salts thereof are required, the unreacted starting materials as principal impurities are in general removed from the reaction product through a recrystallization or extraction method for the purification of the product.

However, when the nuclear-substituted salicylic acids having specific substituents or metal salts thereof are prepared according to Kolbe-Schmitt reactions, the reaction product includes a relatively large amount of the unreacted starting materials. Moreover, the nuclear-substituted salicylic acids or metal salts thereof are in amorphous forms and cannot be purified through recrystallization. Further, they are highly soluble in extraction solvents and have high ability of emulsifying and dispersing aqueous solutions and, therefore, cannot be purified through extraction. Thus, only the reaction product having a low purity could be obtained.

On the other hand, the nuclear-substituted salicylic acids or metal salts thereof prepared according to the method of this invention are used, in particular, in color developing agents for pressure-sensitive recording sheets. However, those prepared by the conventional Kolbe-Schmitt reactions often have low quality and purities and these products as such cannot be satisfactorily used in this application.

SUMMARY OF THE INVENTION

Accordingly, an object of the present invention is to modify and improve the Kolbe-Schmitt reaction conventionally used so as to increase the reaction yield, to improve the purity of the reaction product per se without requiring any further purification and to thus make the product useful as color developing agents for pressure-sensitive recording sheets.

According to the present invention, there is provided a method for preparing a nuclear-substituted salicylic acid or a metal salt thereof represented by the following general formula (1):

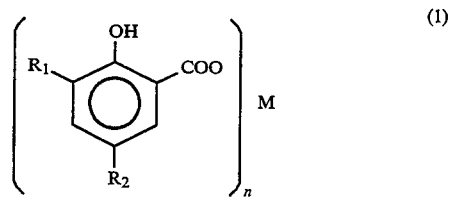

wherein $R_1$ and $R_2$ each represents a t-butyl group, a t-amyl group, a t-octyl group, an isononyl group or an isododecyl group, provided that at least one of $R_1$ and $R_2$ represents an isononyl group or an isododecyl group; M represents a hydrogen atom or a metal atom; and n is the atomic valency of the metal atom M which comprises the step of subjecting, to a Kolbe-Schmitt reaction, an alkali metal salt of a nuclear-substituted phenol represented by the following general formula (2):

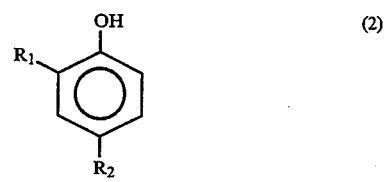

wherein $R_1$ and $R_2$ are the same as those defined above in which 100 to 50% of the alkali metal salt is potassium salt and 0 to 50% thereof is sodium salt, in a substantially water-insoluble solvent as a reaction medium.

The nuclear-substituted salicylic acid or a metal salt thereof prepared according to this method has high purity without any particular purification treatment and thus can satisfactorily be used in all of the intended applications without any post-treatment.

DESCRIPTION OF THE PREFERRED EMBODIMENTS

The method according to the present invention will be explained in more detail below.

In the foregoing general formulae (1) and (2), $R_1$ and $R_2$ each represents a t-butyl group, a t-amyl group, a t-octyl group, an isononyl group or an isododecyl group, provided that at least one of $R_1$ and $R_2$ represents an isononyl group or an isododecyl group. The term "isononyl group" or "isododecyl group" is herein defined to be a group formed through addition of a trimer of propylene (isononene) or a tetramer of propylene (isododecene) to a nucleus of phenol or salicylic acid, respectively. These groups are limited to the foregoing specific ones for the improvement in the color developing density, color developing rate during recording at a low temperature, resistance to light or resistance to water of recorded images when the nuclear-substituted salicylic acid or metal salt thereof is used as a color developing agent for a pressure-sensitive recording sheet and thus, all of these groups are those referred to as tertiary alkyl groups. In addition, at least one of $R_1$ and $R_2$ represents an isononyl group or an isododecyl group. This is because the nuclear-substituted salicylic acid or metal salt thereof carrying such a group is in an amorphous form and most suitable for use as a color developing agent for pressure-sensitive recording sheets. As has been known in this field, both trimer and tetramer of propylene are mixtures comprising a variety of isomers thereof and the nuclear-substituted phenol and nuclear-substituted salicylic acid are likewise mixtures comprising a variety of isomers thereof. It is thus assumed that the amorphousness of these substances is attributable to this fact. The compounds represented by the foregoing general formulae (1) and (2) would always be in amorphous forms if at least one of $R_1$ and $R_2$ represents an isononyl group or an isododecyl group.

Among the nuclear-substituted phenols represented by the general formula (2), specific examples preferably used in the present invention include 2-t-butyl-4-isononylphenol, 2-isononyl-4-t-butylphenol, 2-t-butyl-4-isododecylphenol, 2-isododecyl-4-t-butylphenol, 2-t-amyl-4-isononylphenol, 2-t-octyl-4-isononylphenol, 2-isononyl-4-t-octylphenol, 2,4-diisononylphenol and 2,4-diisododecylphenol, with 2,4-diisononylphenol being most preferred.

All of these nuclear-substituted phenols can form salts with alkali metals. The formation of such a salt most smoothly and completely proceeds when a nuclear-substituted phenol and an aqueous alkali hydroxide solution are mixed in a substantially water-insoluble solvent as a reaction medium and then the water is azeotropically removed. At this stage, it is preferred to use the nuclear-substituted phenol and the alkali hydroxide in absolutely equimolar amounts. Any excess of the alkali hydroxide and water remaining in the reaction system becomes a cause of a reduction of the yield of the Kolbe-Schmitt reaction. The term "substantially water-insoluble solvent" herein means a solvent having a solubility in water of not more than 2% by weight at room temperature. Substantially water-insoluble solvents preferably used in the present invention are, for instance, hydrocarbons, halogenated hydrocarbons and ethers. Moreover, these solvents preferably have a boiling point of not less than 60° C. and not more than 200° C. as determined at atmospheric pressure for the purposes of azeotropically removing the water to give an alkali metal salt of the nuclear-substituted phenol and of removing the solvent from the reaction system after the completion of the Kolbe-Schmitt reaction. Specific examples of such solvents are n-hexane, n-heptane, n-octane, isooctane, n-decane, petroleum benzine, ligroine, petroleum spilit, petroleum naphtha, isononene, isododecene, cyclohexane, methyl cyclohexane, benzene, toluene, xylene, ethylbenzene, diethylbenzene, isopropylbenzene, p-cymene, naphthalene, tetralin, decalin, dipentene, oil of turpentine, chlorobenzene, dichlorobenzene, chlorotoluene, isopropyl ether, n-butyl ether, diisoamyl ether, anisole and ethyl phenyl ether.

The alkali metal salt of the nuclear-substituted phenol obtained by azeotropically removing water while using a substantially water-insoluble sovent as a reaction medium can be subjected to the Kolbe-Schmitt reaction without any post-treatment. The Kolbe-Schmitt reaction is carried out at a carbon dioxide pressure of 1 to 60 Kgf/cm$^2$ and the reaction temperature preferably ranges from 80° to 180° C.

In the conventional methods for preparing salicylic acid or nuclear-substituted salicylic acids through the Kolbe-Schmitt reaction, sodium salts have exclusively been used as alkali metal salts of phenol or nuclear-substituted phenols and potassium salts have never been used. This is because the potassium salts are more expensive than the sodium salts and the reaction rate achieved by the former is slower than that attained by the latter. More specifically, the price of potassium hydroxide is 3 to 4 times higher than that of sodium hydroxide and the reaction rate achieved by the sodium salt is 2 to 4 times greater than that achieved by the potassium salt. However, when the intended specific nuclear-substituted salicylic acids or metal salts thereof are formed from the corresponding alkali metal salts of nuclear-substituted phenols through the Kolbe-Schmitt reaction, the rate of conversion of the starting compound into the intended product is at highest about 80% for sodium salts, while it is easy to achieve a rate of conversion of equal to or more than 90% when potassium salts are used. The reason why potassium salts can provide such high conversions has not yet been clealy elucidated, but this would be resulted from a great difference in solubility in a reaction solvent used between the dialkali metal salts formed during the reaction. In other words, the nuclear-substituted salicylic acid prepared according to the present invention is a mixture comprising a variety of isomers thereof as has been described above, and when a sodium salt of a nuclear-substituted phenol is used, a part of the resulting sodium salt is a disodium salt and a disodium salt a certain substance of the isomers is highly crystalline in nature and hardly soluble in the solvent, the crystalline salt is released outside the reaction system, the reaction system is thus short of alkalis and accordingly, the rate of conversion is reduced. This is also confirmed by the fact that the transparency of the reaction mixture comprising a potassium salt slightly differs from that of the reaction mixture comprising a sodium salt.

Although it is most effective to use a potassium salt in the Kolbe-Schmitt reaction in order to accomplish the purposes of the present invention, i.e., the improvement in the reaction yield or rate of conversion and the formation of a reaction product having high quality, the achievement of the highest rate of conversion within a limited time period requires a further contrivance. Since the Kolbe-Schmitt reaction is an exothermic and equilibrium reaction, the lower the reaction temperature, the higher the carbon dioxide gas pressure and the higher the concentrations of the starting materials in the reaction system, the closer the equilibrium point to the formation system and the higher the rate of conversion achieved, in the light of the teachings of the chemical equilibrium theory. However, the rate of conversion was not significantly influenced by the carbon dioxide gas pressure and the concentrations of the starting materials in the reaction system, although it was improved by the use of a low reaction temperature while extending the reaction time. Thus, a high yield of the nuclear-substituted salicylic acid which has never been achieved through the use of a sodium salt can be obtained when a potassium salt of the nuclear-substituted phenol is subjected to the Kolbe-Schmitt reaction, but it requires a substantially long reaction time to achieve a well-satisfied result. The rates of the Kolbe-Schmitt reaction for sodium salt and potassium salt were determined at 100° C. and it was found that the rate achieved by the use of sodium salt was 3.4 times higher than that achieved by the use of potassium salt. The rate observed for a mixture comprising 10 mole % of a sodium salt and 90 mole % of a potassium salt was found to be 2.9 times that attained through the use of a potassium salt alone. The presence of a sodium salt in such a small amount only slightly affects the rate of conversion and, therefore, a mixture of a sodium salt and a potassium salt can be used for accelerating the rate of the Kolbe-Schmitt reaction. The amount of the sodium salt is preferably not more than 50 mole % and more preferably not more than 20 mole % since the presence of the sodium salt tends to reduce the rate of conversion. The rate of the Kolbe-Schmitt reaction is greatly influenced by the reaction temperature. For instance, the reaction rate observed at 120° C. is 6 times greater than that observed at 100° C. when a potassium salt is used. However, the ultimate rate of conversion is reduced as the reaction temperature increases. Therefore, it is preferred to initially carry out the Kolbe-Schmitt reaction at a relatively high temperature and to subsequently complete the reaction at a low temperature. This allows the achievement of a high rate of conversion within a relatively short period of time. Thus, the reaction temperature preferably ranges from 80° to 180° C. and more preferably the initial reaction temperature is set at a level higher than that at the end of the reaction.

The reaction mixture obtained through the Kolbe-Schmitt reaction comprises an alkali metal salt of a nuclear-substituted salicylic acid. The mixture can easily be converted into the intended nuclear-substituted salicylic acid or metal salt thereof through a simple treatment such as precipitation with an acid or multiple decomposition. Metals preferably used for forming the metal salts thereof include, for instance, sodium, potassium, magnesium, calcium, zinc, aluminum, nickel and cobalt. The products obtained according to the method of the present invention are used, in particular, in color developing agents for pressure-sensitive recording sheets. In this application, polyvalent metal salts, in particular, zinc salts of nuclear-substituted salicylic acids are preferably employed. Among the nuclear-substituted salicylic acids or metal salts thereof specified in the present invention, 3,5-diisononylsalicylic acid or metal salts thereof are most preferred for use in color developing agents for pressure-sensitive recording sheets. The reaction mixture obtained through the Kolbe-Schmitt reaction which is used in a color developing agent for pressure-sensitive recording sheets is subsequently subjected to multiple decomposition to convert the mixture into a polyvalent metal salt of the nuclear-substituted salicylic acid. At this stage, the substantially water-insoluble solvent used as a reaction medium for the Kolbe-Schmitt reaction dissolves the polyvalent metal salt of the nuclear-substituted salicylic acid and is easily separated from the water used for the multiple decomposition and an inorganic salt formed during the decomposition. Therefore, the reaction mixture as such is subjected to the multiple decomposition. Moreover, the unreacted starting material present in the Kolbe-Schmitt reaction system is converted into the nuclear-substituted phenol at this stage, dissolved in the solvent and is not separated from the polyvalent metal salt of the nuclear-substituted salicylic acid. When the reaction product thus obtained is used in a color developing agent for pressure-sensitive recording sheets, the unreacted starting material, i.e., the nuclear-substituted phenol serves to reduce the softening point of the color developer and to accelerate the color developing velocity of the pressure-sensitive recording sheet at a low temperature. On the other hand, if the amount thereof in the product is excessively high, the resulting pressure-sensitive recording sheet tends to cause yellowing due to light rays or nitrogen oxides and the storage stability of a water dispersion of the color developer is often impaired. For this reason, the amount of the nuclear-substituted phenol in the color developer should be preferably limited to not more than 20% by weight and more preferably not more than 15% by weight. Thus, according to the method of the present invention, the amount of the nuclear-substituted phenol as the unreacted material present in the reaction product obtained through the Kolbe-Schmitt reaction can be controlled to a desired range suitable for use in color developing agents for pressure-sensitive recording sheets without removing the unreacted material. Alternatively, the nuclear-substituted phenol may be added to the reaction product after the Kolbe-Schmitt reaction to make the content thereof constant and to thus ensure the quality of the resulting color developer.

The polyvalent metal salts, in particular, zinc salts of the nuclear-substituted salicylic acid exhibit various properties suitable for use in color developing agents for pressure-sensitive recording sheets such as resistance to light, resistance to water, color developing rate at a low temperature, color developing density, stability of images, resistance to background contamination due to sunlight and/or nitrogen oxides. The color developing agents may further comprise other color developing agents, polymeric compounds, UV absorbers, UV stabilizers, antioxidants and/or plasticizers to further improve these properties and to ensure the quality desired for the color developer.

A color developer for pressure-sensitive recording sheet is in general used in the form of fine particles having a particle size ranging from 0.5 to 5 $\mu$m. A color developing composition comprising, as a principal ingredient, a polyvalent metal salt of the nuclear-substituted salicylic acid according to the present invention has a relatively low softening point and, therefore, it is difficult to pulverize it into desired fine particles by the conventional mechanical method. Most preferably, a solution of the color developing composition in an organic solvent is emulsified and dispersed in water containing a dispersant and the organic solvent is optionally removed by distillation to control the particle size thereof. As such a dispersant, there may be used, for instance, an anionic surfactant, polyvinyl alcohol or an acrylamide copolymer. Most preferred organic solvent is the solvent used as a medium for the Kolbe-Schmitt reaction, but other solvents may likewise be used depending on particular purposes. Thus, the color developing composition is most desirably provided as a water dispersion.

In order to make the present invention more apparent, it will be explained in more detail below with reference to the following non-limitative working Examples and Comparative Examples. In the following Examples, the term "%" means "% by weight" unless otherwise specified.

EXAMPLE 1-1

To a 1,000 ml volume four-necked flask of hard glass equipped with a stirring machine, a thermometer, a reflux condenser provided with a device for separating water and a dropping funnel, there were added 276 g (1 mole) of a mixture comprising 91 mole % of 2-t-butyl-4-isononylphenol, 6 mole % of 2-isononyl-4-t-butylphenol and 3 mole % of unknown substances (which have molecular weights identical to the foregoing two components, but do not form salts with alkali metals) and 220 g of xylene. The flask was heated with stirring and immediately after the contents of the flask started boiling, 108.6 g (0.97 mole) of a 50% aqueous solution of potassium hydroxide was dropwise added slowly to the flask through the dropping funnel. The water separated by the reflux condenser during the addition was removed successively. After completion of the dropwise addition of the potassium hydroxide aqueous solution, the dehydration operation was continued till water was not separated any more in the reflux condenser. The contents of the flask were transferred to a 500 ml stainless steel autoclave to such an extent that the contents occupied about 80% of the volume of the autoclave. The autoclave filled with the contents was sealed, the reaction temperature was programmed in such a manner that the contents were heated initially at 140° C. for 2 hours, then at 120° C. for 4 hours and finally at 100° C. for 8 hours and the reaction was carried out at a carbon dioxide gas pressure of 25 Kgf/cm$^2$. The autoclave was cooled, the pressure was released when the temperature of the contents reached not more than 60° C. and the contents was sampled to perform analysis of the same. It was found that the reaction mixture in the autoclave was a xylene solution comprising 91 mole % of the sum of potassium 3-t-butyl-5-isononylsalicylate and potassium 3-isononyl-5-t-butylsalicylate, 6 mole % of the sum of the unreacted starting materials and 3 mole % of the unknown substances. This was subsequently converted into the corresponding nuclear-substituted salicylic acid or metal salts thereof through an appropriate treatment.

EXAMPLE 1-2

To the reaction mixture obtained in Example 1-1, there was added 500 ml of water and the mixture was sufficiently stirred. The mixture was separated into a lower aqueous phase and an upper oil phase when allowing it to stand at 80° C. After the removal of the aqueous phase, 600 g of a 15% aqueous solution of zinc sulfate was added and the mixture was again vigorously stirred at 80° C. for one hour. Thereafter, the mixture was separated into a lower aqueous phase and an upper oil phase containing a zinc nuclear-substituted salicylate when allowing it to stand at this temperature. The oil phase was collected and the content of non-volatile matter thereof was determined by distillation of the oil phase at 100° C. and 20 Torr for 8 hours and was found to be 60.3%. The non-volatile matter comprised 92.6% of the sum of zinc 3-t-butyl-5-isononyl salicylate and zinc 3-isononyl-5-t-butyl salicylate, 5.0% of the sum of the unreacted starting materials and 2.4% of the unknown substances. To 166 g of the oil phase (the content of the non-volatile matter present therein was 100 g), there was added 140 g of an aqueous solution containing 1.5 g of a butyl ac rylate/acrylamide copolymer, 1.5 g of a polyvinyl alcohol having a degree of saponification of 98% and 0.2 g of sodium carbonate, followed by emulsification and dispersion of the mixture by means of a homomixer (Model TK-M; available from Tokushukikakogyo Co., Ltd.) to give a dispersion having an average particle size of 1.15 μm. To the resulting emulsified dispersion, there was added 50 g of water, followed by transfer of the mixture to a flask, heating with gently stirring and azeotropic removal of xylene and water. The amount of these liquids were controlled so that the content of the non-volatile matter present in the resulting water dispersion was 40%. The average particle size of the dispersed phase in the resulting dispersion was found to be 1.0 μm.

COMPARATIVE EXAMPLE 1

A reaction mixture was prepared by repeating the same procedures used in Example 1-1 except that 77.6 g of a 50% aqueous solution of sodium hydroxide was substituted for 108.6 g of the 50% aqueous solution of potassium hydroxide used in Example 1-1. The resulting mixture was a xylene solution containing 73 mole % of the sum of sodium 3-t-butyl-5-isononyl salicylate and sodium 3-isononyl-5-t-butyl salicylate, 24 mole % of the unreacted starting materials and 3 mole % of unknown substances. This was converted into a zinc salt of nuclear-substituted salicylate comprising 77.5% of zinc nuclear-substituted salicylate, 20.1% of the unreacted nuclear-substituted phenol and 2.4% of unknown substances and an aqueous dispersion thereof as a color developing agent for pressure-sensitive recording sheets was prepared in the same manner used in Example 1-2. The viscosity of the dispersion was liable to increase during the storage stability test performed at 35° C. as compared with the dispersion of Example 1-2 and thus the former was judged to be inapplicable as a color developer for pressure-sensitive recording sheets.

EXAMPLE 2

To a flask identical to that used in Example 1-1, there were added 232 g (0.67 mole) of a mixture comprising 97 mole % of 2,4-diisononylphenol and 3 mole % of an unknown substance (which has a molecular weight identical to 2,4-diisononylphenol, but does not form salts with alkali metals) and 170 g of xylene. The flask was heated with stirring and immediately after the contents of the flask started boiling, 72.9 g (0.65 mole) of a 50% aqueous solution of potassium hydroxide was dropwise added slowly to the flask through the dropping funnel. After completion of the dehydration performed in the same manner used in Example 1-1, whole of the contents of the flask were transferred to an autoclave identical to that used in Example 1-1. The autoclave filled with the contents was sealed, the reaction was performed at 100° C. and a carbon dioxide gas pressure of 50 Kgf/cm$^2$. In the course of the reaction, the contents were sampled (4, 8 and 12 hours after the initiation of the reaction) for the determination of the reaction rate or the rate of conversion and the rates of conversion were found to be 21.9% (after 4 hours), 39.4% (after 8 hours) and 52.4% (after 12 hours). It was confirmed, from the determination of these rates of conversion, that this reaction is a first-order reaction under these conditions. The reaction was further continued till the overall reaction time reached 96 hours and then the autoclave was cooled to remove the reaction mixture. It was found that the reaction mixture in the autoclave was a xylene solution comprising 91.5 mole % of potassium 3,5-diisononylsalicylate, 5.5 mole % of unreacted 2,4-diisononylphenol and 3 mole % of the unknown substance. Then the reaction mixture was subjected to multiple decomposition in the same manner used in Example 1-2, followed by allowing to stand and separation of the upper oil phase. The content of non-volatile matter in the oil phase was determined in the same manner used in Example 1-2 and was found to be 60.5%. Then, to 165 g of the oil phase (the content of the non-volatile matter present therein was 100 g), there was added 3.0 g of 2,4-diisononylphenol, followed by emulsification and dispersion, and removal of the solvent in the same manner used in Example 1-2 to prepare an aqueous dispersion of a color developer for pressure-sensitive recording sheets mainly comprising zinc 3,5-diisononylsalicylate (90.0% of zinc 3,5-diisononylsalicylate, 7.5% of 2,4-diisononylphenol and 2.5% of the unknown substance).

COMPARATIVE EXAMPLE 2

The same procedures use in Example 2 were repeated except that 52 g (0.65 mole) of a 50% sodium hydroxide aqueous solution was substituted for 72.9 g (0.65 mole) of the 50% aqueous solution of potassium hydroxide to thus complete dehydration. The contents of the flask were transferred to an autoclave identical to that used in Example 2 and the reaction was performed at 100° C. and a carbon dioxide gas pressure of 50 Kgf/cm$^2$. In the course of the reaction, the contents were sampled (1, 2 and 3 hours after the initiation of the reaction) for the determination of the reaction rate or the rate of conversion and the rates of conversion were found to be 20.2% (after 1 hour), 35.2% (after 2 hours) and 47.4% (after 3 hours). It was confirmed, from the determination of these rates of conversion, that this reaction is a first-order reaction under these conditions like the reaction in Example 2. However, the rate of the reaction was 3.4 times faster than that observed in Example 2. It was assumed, from this fact, that the reaction time of 28 hours is sufficient for achieving the results similar to those observed in Example 2 at the reaction time of 96 hours. Thus, after 32 hours, the autoclave was cooled to remove the contents thereof. It was found that the reaction mixture in the autoclave was a xylene solution comprising 76.4 mole % of sodium 3,5-diisononylsalicylate, 20.6 mole % of unreacted 2,4-diisononylphenol and 3 mole % of unknown substances. Then the reaction mixture was treated in the same manner used in Example 1-2 to give an aqueous dispersion of a color developer for pressure-sensitive recording sheets (79.6% of zinc 3,5-diisononylsalicylate, 17.8% of 2,4-diisononylphenol and 2.6% of the unknown substance). The aqueous dispersions prepared in Example 2 and Comparative Example 2 were subjected to a storage stability test at 35° C. and it was found that the viscosity of the dispersion of Comparative Example 2 was liable to significantly increase as compared with the dispersion of Example 2. In addition, pressure-sensitive recording sheets were finished using these aqueous dispersions and the sheet treated with the dispersion of Comparative Example was inferior in the color developing density and resistance to yellowing due to sunlight and/or nitrogen oxides to that treated with the dispersion of Example 2.

EXAMPLE 3

The same procedures used in Example 2 were repeated to give a dehydrated xylene solution of potassium salt of 2,4-diisononylphenol. The solution was transferred to an autoclave identical to that used in Example 2 and reacted at 120° C. and a carbon dioxide gas pressure of 50 Kgf/cm$^2$. The content of the autoclave was sampled in the course of the reaction (1 and 2 hours after the initiation of the reaction) to determine the rate of conversion and these rates of conversion were found to be 32.0% (after one hour) and 51.9% (after 2 hours). This indicates that the reaction rate is just 6 times that observed in Example 2 and therefore, it is assumed that the reaction time of 16 hours is sufficient for achieving the results similar to those observed in Example 2 at the reaction time of 96 hours. Thus, after 24 hours, the autoclave was cooled to remove the contents thereof. It was found that the reaction mixture in the autoclave was a xylene solution comprising 88.6 mole % of potassium 3,5-diisononylsalicylate, 8.4 mole % of unreacted 2,4-diisononylphenol and 3 mole % of the unknown substance. Then the reaction mixture was treated in the same manner used in Example 1-2 to give an aqueous dispersion of a color developer for pressure-sensitive recording sheets (90.2% of zinc 3,5-diisononylsalicylate, 7.1% of 2,4-diisononylphenol and 2.7% of the unknown substance).

EXAMPLE 4

The same procedures used in Example 2 were repeated to give a dehydrated xylene solution of potassium salt of 2,4-diisononylphenol. The solution was transferred to an autoclave identical to that used in Example 2 and the reaction temperature was programmed in such a manner that the solution was reacted initially at 140° C. for 2 hours, then at 120° C. for 4 hours and finally at 100° C. for 18 hours (the overall reaction time was set at 24 hours) and it was reacted at a carbon dioxide gas pressure of 50 Kgf/cm$^2$. It was found that the reaction mixture was a xylene solution comprising 91.3 mole % of potassium 3,5-diisononylsalicylate, 5.7 mole % of unreacted 2,4-diisononylphenol and 3 mole % of the unknown substance. In other words, the results obtained were almost the same as those obtained in Example 2. Then the reaction mixture was treated in the same manner used in Example 1-2 to give an aqueous dispersion of a color developer for pressure-sensitive recording sheets (92.6% of zinc 3,5-diisononylsalicylate, 4.9% of 2,4-diisononylphenol and 2.5% of the unknown substance).

EXAMPLE 5

To a flask identical to that used in Example 2, there were added 232 g (0.67 mole) of a mixture comprising 97 mole % of 2,4-diisononylphenol and 3 mole % of an unknown substance and 170 g of xylene. The flask was heated with stirring and immediately after the contents of the flask started boiling, 65.6 g (0.585 mole) of a 50% aqueous solution of potassium hydroxide was dropwise added slowly to the flask through the dropping funnel. After the dropwise addition, 5.2 g (0.065 mole) of a 50% aqueous solution of sodium hydroxide was dropwise added thereto. The dehydrated mixture was transferred to an autoclave identical to that used in Example 2 and the reaction was performed at 100° C. and a carbon dioxide gas pressure of 50 Kgf/cm$^2$. In the course of the reaction, the contents were sampled (1, 2 and 4 hours after the initiation of the reaction) for the determination of the rate of conversion and the rates of conversion were found to be 15.3% (after 1 hours), 29.1% (after 2 hours) and 48.7% (after 4 hours). It was confirmed that this reaction is also a first-order reaction under these conditions. The reaction rate was 2.8 times that observed in Example 2 and 0.8 time that observed in Comparative Example 2. Therefore, it is assumed that the reaction time of 34 hours is sufficient for achieving the results similar to those observed in Example 2 at the reaction time of 96 hours. Thus, after 40 hours, the autoclave was cooled to remove the reaction mixture. It was found that the reaction mixture was a xylene solution comprising 88.7 mole % of 3,5-diisononylsalicylic acid salt, 8.3 mole % of unreacted 2,4-diisononylphenol and 3 mole % of the unknown substance. Then the reaction mixture was treated in the same manner used in Example 1-2 to give an aqueous dispersion of a color developer for pressure-sensitive recording sheets (90.3% of zinc 3,5-diisononylsalicylate, 7.0% of 2,4-diisononylphenol and 2.7% of the unknown substance).

EXAMPLE 6

The same procedures used in Example 2 were repeated except that 170 g of toluene was substituted for 170 g of xylene used in Example 2 to give a toluene solution of potassium salt of 2,4-diisononylphenol. The dehydrated solution was transferred to an autoclave identical to that used in Example 2, the reaction temperature and time were programmed in such a manner that the solution was reacted initially at 140° C. for 2 hours, then at 120° C. for 4 hours and finally at 100° C. for 18 hours and it was reacted at a carbon dioxide gas pressure of 20 Kgf/cm$^2$. It was found that the reaction mixture obtained after completion of the reaction was a toluene solution comprising 90.3 mole % of potassium 3,5-diisononylsalicylate, 6.7 mole % of unreacted 2,4-diisononylphenol and 3 mole % of the unknown substance. Surprisingly, it was found that the rate of conversion was not inferior to that observed in Example 2 and that the effect of the carbon dioxide gas pressure was not significant. Then the reaction mixture was treated in the same manner used in Example 1-2 to give an aqueous dispersion of a color developer for pressure-sensitive recording sheets (91.8% of zinc 3,5-diisononylsalicylate, 5.7% of 2,4-diisononylphenol and 2.5% of the unknown substance).

EXAMPLE 7

To a flask identical to that used in Example 4, there were added 223 g (0.7 mole) of a mixture comprising 99.2 mole % of 2-isododecyl-4-t-butylphenol and 0.8 mole % of an unknown substance (which has a molecular weight identical to the phenol, but does not form salts with alkali metals) and 170 g of xylene. Then 77.8 g (0.693 mole) of a 50% aqueous solution of potassium hydroxide was dropwise added to the flask through the dropping funnel and then the mixture was treated according to the same procedures used in Example 4 to give a reaction mixture. It was found that the reaction mixture was a xylene solution comprising 92.8 mole % of potassium 3-isododecyl-5-t-butylsalicylate, 6.4 mole % of unreacted 2-isododecyl-4-t-butylphenol and 0.8 mole % of the unknown substance. Then the reaction mixture was treated in the same manner used in Example 1-2 to give an aqueous dispersion of a color developer for pressure-sensitive recording sheets (94.0% of zinc 3-isododecyl-5-t-butylsalicylate, 5.4% of 2-isododecyl-4-t-butylphenol and 0.6% of the unknown substance).

COMPARATIVE EXAMPLE 3

The same procedures used in Example 7 were repeated except that 55.4 g (0.693 mole) of a 50% aqueous solution of sodium hydroxide was substituted for 77.8 g of the 50% aqueous solution of potassium hydroxide used in Example 7 to give a xylene solution comprising 75.4 mole % of sodium 3-isododecyl-5-t-butylsalicylate, 23.8 mole % of unreacted 2-isododecyl-4-t-butylphenol and 0.8 mole % of the unknown substance. Then the reaction mixture was treated in the same manner used in Example 1-2 to give an aqueous dispersion of a color developer for pressure-sensitive recording sheets (79.1% of zinc 3-isododecyl- 5-t-butylsalicylate, 20.3% of 2-isododecyl-4-t-butylphenol and 0.6% of the unknown substance).

EXAMPLE 8-1

To a flask identical to that used in Example 1-1, there were added 194.3 g (0.67 mole) of a mixture comprising 98.2 mole % of the sum of 2-t-amyl-4-isononylphenol and 2-isononyl-4-t-amylphenol and 1.8 mole % of unknown substances (which have molecular weights identical to the foregoing phenols, but do not form salts with alkali metals) and 170 g of xylene. The flask was heated with stirring and immediately after the contents of the flask started boiling, 73.8 g (0.658 mole) of a 50% aqueous solution of potassium hydroxide was dropwise added slowly to the flask through the dropping funnel. The dehydration of the solution was completed in the same manner used in Example 1-1. The solution was treated in the same manner used in Example 1-1 to give a xylene solution comprising 91.3 mole % of the sum of potassium 3-t-amyl-5-isononylsalicylate and potassium 3-isononyl-5-t-amylsalicylate, 6.9 mole % of the sum of unreacted 2-t-amyl-4-isononylphenol and 2-isononyl-4-t-amylphenol and 1.8 mole % of the unknown substances.

EXAMPLE 8-2

The reaction mixture prepared in Example 8-1 was treated in the same manner used in Example 1-2 to give an aqueous dispersion having a content of non-volatile matter of 40% and an average particle size of the dispersed phase of 1.0 $\mu$m. The dispersed phase comprised 93.0% of the sum of zinc 3-t-amyl-5-isononylsalicylate and zinc 3-isononyl-5-t-amylsalicylate, 5.6% of the sum of 2-t-amyl-4-isononylphenol and 2-isononyl-4-t-amylphenol and 1.4% of the unknown substances.

COMPARATIVE EXAMPLE 4

The same procedures used in Example 8-1 were repeated except that 52.6 g of a 50% aqueous solution of sodium hydroxide was substituted for 73.8 g of the 50% aqueous solution of potassium hydroxide to give a xylene solution comprising 73.5 mole % of the sum of sodium 3-t-amyl-5-isononylsalicylate and sodium 3-isononyl-5-t-amylsalicylate, 24.7 mole % of the sum of unreacted 2-t-amyl-4-isononylphenol and 2-isononyl-4-t-amylphenol and 1.8 mole % of unknown substances. Then the same procedures used in Example 8-2 were repeated to give an aqueous dispersion of a color developer for pressure-sensitive recording sheets. The dispersed phase comprised 77.8% of the sum of zinc 3-t-amyl-5-isononylsalicylate and zinc 3-isononyl-5-t-amylsalicylate, 20.7% of the sum of 2-t-amyl-4-isononylphenol and 2-isononyl-4-t-amylphenol and 1.5% of the unknown substances.

EXAMPLE 9

The same procedures used in Example 2 were repeated except that 222 g of a mixture comprising 98.1 mole % of 2-isononyl-4-t-octylphenol and 1.9 mole % of an unknown substance (which has a molecular weight identical to that of 2-isononyl-4-t-octylphenol, but does not form salts with alkali metals) was substituted for 232 g of the mixture comprising 97 mole % of 2,4-diisononylphenol and 3 mole % of the unknown substance and that the amount of the 50% aqueous potassium hydroxide solution used was changed from 72.9 g to 73.7 g to give a reaction mixture which comprised 90.7 mole % of potassium 3-isononyl-5-t-octylsalicylate, 7.6 mole % of unreacted 2-isononyl-4-t-octylphenol and 1.9 mole % of the unknown substance. The reaction mixture was treated in the same manner to prepare an aqueous dispersion of a color developer for pressure-sensitive recording sheets comprising 92.1% zinc 3-isononyl-5-t-octylsalicylate, 6.3% 2-isononyl-4-t-octylphenol and 1.6% of the unknown substance.

COMPARATIVE EXAMPLE 5

The same procedures used in Example 9 were repeated except that 52.5 g of a 50% aqueous solution of sodium hydroxide was substituted for 73.7 g of the 50% aqueous solution of potassium hydroxide to give a reaction mixture comprising 74.6 mole % of sodium 3-isononyl-5-t-octylsalicylate, 23.5 mole % of 2-isononyl-4-t-octylphenol and 1.9 mole % of an unknown substance. Then the reaction mixture was treated in the same manner to give an aqueous dispersion of a color developer for pressure-sensitive recording sheets which comprised 78.3% of zinc 3-isononyl-5-t-octylsalicylate, 20.1% of 2-isononyl-4-t-octylphenol and 1.6% of the unknown substance.

EXAMPLE 10

Storage Stability Test of Aqueous Dispersion

There were collected 80 g each of the aqueous dispersions having the content of non-volatile matter of 40% and comprising dispersed phases having an average particle size of 1 μm, prepared in Examples 1-2, 2, 3, 4, 5, 6, 7, 8-2 and 9 and Comparative Examples 1, 2, 3, 4 and 5 and each sample was introduced into a flask having an inner volume of 100 ml. Each flask was equipped with a stirring machine having a paddle of 2 cm length and 1 cm width and was designed so as to maintain air-tight condition except that it was communicated with the air only through a condenser tube. Each flask was sufficiently immersed in a bath of 35° C. with stirring at 500 rpm. The flasks were allowing to stand for one week under these conditions and then the viscosity of each dispersion was determined. The dispersions initially had viscosities falling within the range of from 15 to 35 cps. The storage stability of these dispersions was evaluated on the basis of the viscosities thereof according to the following four evaluation criteria:

◎: the viscosity observed after the one week storage is not more than 50 cps;

○: the viscosity observed after the one week storage ranges from 50 to 100 cps;

Δ: the viscosity observed after the one week storage ranges from 100 to 500 cps; and x: the viscosity observed after the one week storage is not less than 500 cps.

The results thus obtained are listed in the following Table 1.

EXAMPLE 11

Test for Pressure-sensitive Recording Sheets

Preparation of Coating Liquid of Color Developer

Fourteen coating liquids of color developers each having the following formulation were prepared using 40% aqueous dispersions obtained in Examples 1-2, 2, 3, 4, 5, 6, 7, 8-2 and 9 and Comparative Examples 1, 2, 3, 4 and 5.

To 100 parts by weight of water, there were added 80 parts by weight of calcium carbonate, 25 parts by weight of each 40% dispersion of the color developer and 10 parts by weight of zinc oxide and these ingredients were admixed and uniformly dispersed. Then the mixture was admixed with 50 parts by weight of a 10% polyvinyl alcohol aqueous solution and 10 parts by weight of a carboxy-modified SBR latex (trade name: SN-307; solid content=50%; available from Sumitomo Norgatac Co., Ltd.) followed by uniform dispersion to give coating liquids of the foregoing color developers.

Preparation of Color Developing Paper for Pressure-Sensitive Recording Sheets

Each coating liquid prepared above was applied onto one side of base paper having a basis weight of 40 g/m$^2$ in an amount of 4 g/m$^2$ (weighed after drying) and then dried to give 14 kinds of color developing paper for pressure-sensitive recording sheets.

These 14 kinds of color developing paper for pressure-sensitive recording sheets were subjected to the following quality-evaluation tests. The results obtained are listed in Table 1.

Preparation of Top Sheet

Crystal Violet Lactone was dissolved in an alkylated naphthalene, a microcapsule coating liquid prepared by forming the resulting oily solution into microcapsules was applied onto one side of wood-free paper in an amount of 4 g/m$^2$ (weighed after drying) and then dried to give top sheet.

Test of Color Developability at Low Temperature

The color developing paper and the top sheet prepared above were allowed to stand at 0° C. for 10 hours. Thereafter, the coated surfaces of the color developing paper and the top sheet faced each other and they were color-developed in an atmosphere of 0° C. using a drop-coloring tester (plumb: 150 g; height: 15 cm) and the color density developed 10 seconds after application of the pressure was determined using reflection densitometer (Model RD-914; available from Macbeth Corp., the greater the numerical value thereof, the better the color developing properties).

Color Developing Density

The samples thus color-developed according to the foregoing method were allowed to stand at room temperature (25° C., 65% RH) for 2 days and then the developed color density thereof was again determined by reflection densitometer (the greater the numerical value thereof, the better the quality of the sample).

Light Resistance Test

The coated surfaces of the color developing paper and the top sheet prepared above faced each other and they were color-developed at room temperature using a drop-coloring tester (plumb: 150 g; height: 15 cm). Then they were allowed to stand at room temperature for not less than 12 hours, followed by exposure to sunlight for 8 hours and determination of the developed color density by reflection densitometer (the greater the numerical value thereof, the better the quality of the sample).

Water Resistance Test

Color-developed images were formed by the same method used in the light resistance test and allowed to stand for 5 minutes to give samples. These samples were immersed in water of about 20° C. for 5 hours and then the developed color density was determined by reflection densitometer (the greater the numerical value thereof, the better the quality of the sample).

Yellowing Due to Light

The color developing paper prepared in the same manner used above was exposed to sunlight for 2 days and the degree of yellowing of the color developing layers were visually evaluated according to the following three evaluation criteria:
⊙: Yellowing was not observed at all.
○: Yellowing was slightly observed.
Δ: Substantial yellowing was observed.

TABLE 1

| Ex. No. | S.S. | C.D.L. | C.D.D. | L.R. | W.R. | YE |
|---|---|---|---|---|---|---|
| 1-2 | ⊙ | 0.31 | 0.72 | 0.61 | 0.62 | ⊙ |
| 2 | ⊙ | 0.37 | 0.78 | 0.66 | 0.70 | ⊙ |
| 3 | ⊙ | 0.38 | 0.77 | 0.65 | 0.68 | ⊙ |
| 4 | ⊙ | 0.36 | 0.79 | 0.66 | 0.71 | ⊙ |
| 5 | ⊙ | 0.38 | 0.78 | 0.65 | 0.69 | ⊙ |
| 6 | ⊙ | 0.38 | 0.78 | 0.65 | 0.69 | ⊙ |
| 7 | ⊙ | 0.28 | 0.72 | 0.60 | 0.61 | ⊙ |
| 8-2 | ⊙ | 0.30 | 0.73 | 0.61 | 0.62 | ⊙ |
| 9 | ⊙ | 0.31 | 0.72 | 0.60 | 0.61 | ⊙ |
| 1* | Δ | 0.34 | 0.69 | 0.55 | 0.56 | ○ |
| 2* | ○ | 0.38 | 0.70 | 0.56 | 0.57 | ○ |
| 3* | Δ | 0.30 | 0.68 | 0.53 | 0.54 | ○ |
| 4* | Δ | 0.34 | 0.61 | 0.48 | 0.37 | ○ |
| 5* | Δ | 0.35 | 0.62 | 0.49 | 0.38 | ○ |

1* to 5*: Comparative Example.
S.S.: Storage stability.
C.D.L.: Color developability at low temperature (10 second after).
C.D.D.: Color developing Density.
L.R.: Light resistance.
W.R.: Water resistance.
YE: Yellowing due to light.

The method according to the present invention makes it possible to improve the yield of specific nuclear-substituted salicylic acids and metal salts thereof and to provide such products having high purity without any post-treatment. These compounds can be used as materials for color developing agents for pressure-sensitive recording sheets without any additional purification treatment.

We claim:

1. A color developer for pressure-sensitive recording sheets which comprises at least one polyvalent metal salt of a nuclear-substituted salicylic acid represented by the following general formula (1):

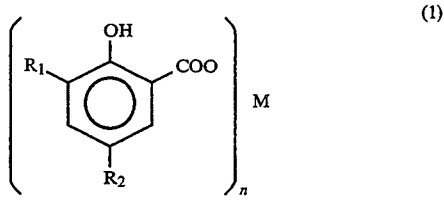

wherein $R_1$ and $R_2$ each represents a t-butyl group, a t-amyl group, a t-octyl group, an isononyl group or an isododecyl group, provided that at least one of $R_1$ and $R_2$ represents an isononyl group or an isododecyl group; M represents a polyvalent metal atom; and n is the atomic valency of the polyvalent metal atom M, said polyvalent metal salt being prepared by subjecting, to a Kolbe-Schmitt reaction, an alkali metal salt of a nuclear-substituted phenol represented by the following general formula (2):

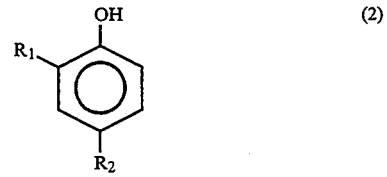

wherein $R_1$ and $R_2$ have the meanings defined above, in which 100 to 50% of the alkali metal salt is potassium salt and 0 to 50% thereof is sodium salt, in a substantially water-insoluble solvent as a reaction medium, and then converting the resultant product into the polyvalent metal salt having said general formula (1) by multiple decomposition.

2. The color developer according to claim 1 wherein the nuclear-substituted phenol represented by the general formula (2) is 2,4-diisononylphenol and the nuclear-substituted salicylic acid or metal salt thereof represented by the general formula (1) is 3,5-diisononyl salicylic acid or metal salt thereof.

3. The color developer according to claim 1 wherein the substantially water-insoluble solvent is selected from the group consisting of hydrocarbons, halogenated hydrocarbons or ethers having a boiling point ranging from 60° to 200° C.

4. The color developer according to claim 3 wherein the nuclear-substituted phenol represented by the general formula (2) is 2,4-diisononylphenol and the nuclear-substituted salicylic acid or metal salt thereof represented by the general formula (1) is 3,5-diisononyl salicylic acid or metal salt thereof.

5. The color developer according to claim 1 wherein the Kolbe-Schmitt reaction is carried out at a temperature ranging from 80° to 180° C.

6. The color developer according to claim 5 wherein the nuclear-substituted phenol represented by the general formula (2) is 2,4-diisononylphenol and the nuclear-substituted salicylic acid or metal salt thereof represented by the general formula (1) is 3,5-diisononyl salicylic acid or metal salt thereof.

7. The color developer according to claim 5 wherein the substantially water-insoluble solvent is selected from the group consisting of hydrocarbons, halogenated hydrocarbons or ethers having a boiling point ranging from 60° to 200° C.

8. The color developer according to claim 1 wherein the alkali metal salt comprises 100 to 80 mole % of potassium salt and 0 to 20 mole % of sodium salt.

9. The color developer according to claim 8 wherein the nuclear-substituted phenol represented by the general formula (2) is 2,4-diisononylphenol and the nuclear-substituted salicylic acid or metal salt thereof represented by the general formula (1) is 3,5-diisononyl salicylic acid or metal salt thereof.

10. The color developer according to claim 8 wherein the substantially water-insoluble solvent is selected from the group consisting of hydrocarbons, halogenated hydrocarbons or ethers having a boiling point ranging from 60° to 200° C.

11. The color developer according to claim 8 wherein the Kolbe-Schmitt reaction is carried out at a temperature ranging from 80° to 180° C.

* * * * *